(12) United States Patent
Gysling (10) Patent No.: US 7,181,955 B2
(45) Date of Patent: *Feb. 27, 2007

(54) APPARATUS AND METHOD FOR MEASURING MULTI-PHASE FLOWS IN PULP AND PAPER INDUSTRY APPLICATIONS

(75) Inventor: Daniel L. Gysling, Glastonbury, CT (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/636,095

(22) Filed: Aug. 7, 2003

(65) Prior Publication Data

US 2004/0074312 A1 Apr. 22, 2004

Related U.S. Application Data

(60) Provisional application No. 60/402,491, filed on Aug. 8, 2002.

(51) Int. Cl.
*G01N 33/34* (2006.01)
*G01N 29/00* (2006.01)

(52) U.S. Cl. .................................. 73/53.03; 73/61.49
(58) Field of Classification Search ............... 73/53.03, 73/19.01, 19.04, 19.1, 24.01, 32 A, 61.44, 73/61.45, 61.49, 64.53
See application file for complete search history.

(56) References Cited

U.S. PATENT DOCUMENTS

| | | | |
|---|---|---|---|
| 3,149,492 A | 9/1964 | Weinberg | |
| 3,781,895 A | 12/1973 | Monser | |
| 3,851,521 A | 12/1974 | Ottenstein | |
| 3,952,578 A | 4/1976 | Jacobs | |

(Continued)

FOREIGN PATENT DOCUMENTS

| WO | WO 14382 | 7/1993 |
|---|---|---|
| WO | WO 0000793 | 1/2000 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

(Continued)

*Primary Examiner*—Michael Cygan
(74) *Attorney, Agent, or Firm*—Patterson & Sheridan, LLP (57) ABSTRACT

The consistency of a pulp slurry in a pipe 12 is determined using a pair of effective sound speeds $a_{1\mathit{eff}}$ and $a_{2\mathit{eff}}$ of the fluid/pipe system. The pair of effective system sound speed measurements are taken at two sensing regions $X_1$, $X_2$ along the pipe wherein each of the sensing regions comprises a different system cross sectional area compliance. The pair of effective system sound speeds $a_{1\mathit{eff}}$ and $a_{2\mathit{eff}}$ are provided to signal processing logic 160, which determines at least the composition of the fluid 12 flowing in the pipe 112. The effective system sound speeds $a_{1\mathit{eff}}$ and $a_{2\mathit{eff}}$ may be provided by a pair of sound speed meters positioned at sensing regions $X_1$, $X_2$ wherein the sound speed meters utilize a spatial array of acoustic pressure sensors placed at predetermined axial locations along the pipe 112. One technique uses acoustic spatial array signal processing techniques with the direction of propagation of the acoustic signals along the longitudinal axis of the pipe 112.

38 Claims, 8 Drawing Sheets

U.S. PATENT DOCUMENTS

| | | | |
|---|---|---|---|
| 4,080,837 A | 3/1978 | Alexander et al. | |
| 4,114,439 A | 9/1978 | Fick | |
| 4,144,768 A | 3/1979 | Anderson | |
| 4,159,646 A | 7/1979 | Paulsen | |
| 4,164,865 A | 8/1979 | Hall | |
| 4,236,406 A | 12/1980 | Reed | |
| 4,275,602 A | 6/1981 | Fujishiro | |
| 4,320,659 A | 3/1982 | Lynnworth et al. | |
| 4,445,389 A | 5/1984 | Potzick et al. | |
| 4,499,418 A | 2/1985 | Helms | |
| 4,515,473 A | 5/1985 | Mermelstein | |
| 4,520,320 A | 5/1985 | Potzick et al. | |
| 4,546,649 A | 10/1985 | Kantor | |
| 4,677,305 A | 6/1987 | Ellinger | |
| 4,706,501 A | 11/1987 | Atkinson | |
| 4,717,159 A | 1/1988 | Alston et al. | |
| 4,788,852 A | 12/1988 | Martin | |
| 4,813,270 A | 3/1989 | Baillie | |
| 4,862,750 A | 9/1989 | Nice | |
| 4,864,868 A | 9/1989 | Khalifa | |
| 4,884,457 A | 12/1989 | Hatton | |
| 4,896,540 A | 1/1990 | Shakkottai et al. | |
| 4,932,262 A | 6/1990 | Wlodarczyk | |
| 4,947,127 A | 8/1990 | Helms | |
| 4,950,883 A | 8/1990 | Glenn | |
| 4,976,151 A | 12/1990 | Morishita | |
| 4,996,419 A | 2/1991 | Morey | |
| 5,024,099 A | 6/1991 | Lee | |
| 5,031,460 A | 7/1991 | Kanenobu | |
| 5,040,415 A | 8/1991 | Barkhoudarian | |
| 5,051,922 A | 9/1991 | Toral | |
| 5,058,437 A | 10/1991 | Chaumont | |
| 5,083,452 A | 1/1992 | Hope | |
| 5,099,697 A | 3/1992 | Agar | |
| 5,115,670 A | 5/1992 | Shen | |
| 5,152,181 A | 10/1992 | Lew | |
| 5,207,107 A | 5/1993 | Wolf | |
| 5,218,197 A | 6/1993 | Carroll | |
| 5,317,576 A | 5/1994 | Leonberger et al. | |
| 5,321,991 A | 6/1994 | Kalotay | |
| 5,347,873 A | 9/1994 | Vander Heyden | |
| 5,359,897 A | 11/1994 | Hamstead et al. | |
| 5,361,130 A | 11/1994 | Kersey | |
| 5,363,342 A | 11/1994 | Layton et al. | |
| 5,367,911 A | 11/1994 | Jewell et al. | |
| 5,372,046 A | 12/1994 | Kleven | |
| 5,392,638 A * | 2/1995 | Kawahara | 73/61.49 |
| 5,398,542 A | 3/1995 | Vasbinder | |
| 5,401,956 A | 3/1995 | Dunphy et al. | |
| 5,426,297 A | 6/1995 | Dunphy et al. | |
| 5,440,932 A | 8/1995 | Wareham | |
| 5,493,390 A | 2/1996 | Varasi et al. | |
| 5,493,512 A | 2/1996 | Peube et al. | |
| 5,513,913 A | 5/1996 | Ball | |
| 5,524,475 A * | 6/1996 | Kolpak et al. | 73/19.03 |
| 5,546,813 A * | 8/1996 | Hastings et al. | 73/861.29 |
| 5,548,530 A | 8/1996 | Baumoel | |
| 5,564,832 A | 10/1996 | Ball | |
| 5,576,497 A | 11/1996 | Vignos | |
| 5,591,922 A | 1/1997 | Segeral et al. | |
| 5,597,961 A | 1/1997 | Marrelli | |
| 5,639,667 A * | 6/1997 | Heslot et al. | 436/148 |
| 5,642,098 A | 6/1997 | Santa Maria | |
| 5,644,093 A | 7/1997 | Wright | |
| 5,654,551 A | 8/1997 | Watt | |
| 5,670,720 A | 9/1997 | Clark | |
| 5,680,489 A | 10/1997 | Kersey | |
| 5,689,540 A | 11/1997 | Stephenson | |
| 5,708,211 A | 1/1998 | Jepson et al. | |
| 5,719,329 A * | 2/1998 | Jepson et al. | 73/61.49 |
| 5,730,219 A | 3/1998 | Tubel | |
| 5,732,776 A | 3/1998 | Tubel | |
| 5,741,980 A | 4/1998 | Hill et al. | |
| 5,770,805 A | 6/1998 | Castel | |
| 5,770,806 A | 6/1998 | Hiismaki | |
| 5,803,167 A | 9/1998 | Bussear | |
| 5,804,713 A | 9/1998 | Kluth | |
| 5,835,884 A | 11/1998 | Brown | |
| 5,842,347 A | 12/1998 | Kinder | |
| 5,845,033 A | 12/1998 | Berthold et al. | |
| 5,906,238 A | 5/1999 | Carmody | |
| 5,907,104 A | 5/1999 | Cage | |
| 5,908,990 A | 6/1999 | Cummings | |
| 5,925,821 A | 7/1999 | Bousquet | |
| 5,925,879 A | 7/1999 | Hay | |
| 5,939,643 A | 8/1999 | Oertel | |
| 5,948,959 A | 9/1999 | Peloquin | |
| 5,956,132 A | 9/1999 | Donzier | |
| 5,959,547 A | 9/1999 | Tubel | |
| 5,963,880 A | 10/1999 | Smith | |
| 5,975,204 A | 11/1999 | Tubel | |
| 5,992,519 A | 11/1999 | Ramakrishnan | |
| 5,996,690 A | 12/1999 | Shaw | |
| 6,002,985 A | 12/1999 | Stephenson | |
| 6,003,383 A | 12/1999 | Zielinska | |
| 6,003,385 A | 12/1999 | De Vanssay | |
| 6,009,216 A | 12/1999 | Pruett | |
| 6,016,702 A | 1/2000 | Maron | |
| 6,158,288 A | 12/2000 | Smith | |
| 6,202,494 B1 | 3/2001 | Riebel et al. | |
| 6,216,532 B1 | 4/2001 | Stephenson | |
| 6,233,374 B1 | 5/2001 | Ogle | |
| 6,279,660 B1 | 8/2001 | Hay | |
| 6,286,360 B1 * | 9/2001 | Drzewiecki | 73/24.01 |
| 6,349,599 B1 | 2/2002 | Lynnworth et al. | |
| 6,354,147 B1 * | 3/2002 | Gysling et al. | 73/61.79 |
| 6,371,982 B2 | 4/2002 | Berg | |
| 6,378,357 B1 | 4/2002 | Han et al. | |
| 6,435,030 B1 | 8/2002 | Gysling et al. | |
| 6,442,996 B1 | 9/2002 | Thurston et al. | |
| 6,446,494 B2 | 9/2002 | Hastings | |
| 6,450,037 B1 | 9/2002 | McGuinn et al. | |
| 6,463,813 B1 | 10/2002 | Gysling | |
| 6,502,465 B1 * | 1/2003 | Vedapuri et al. | 73/861.04 |
| 6,536,291 B1 | 3/2003 | Gysling et al. | |
| 6,550,342 B2 | 4/2003 | Croteau et al. | |
| 6,587,798 B2 | 7/2003 | Kersey et al. | |
| 6,601,458 B1 | 8/2003 | Gysling et al. | |
| 6,609,069 B2 | 8/2003 | Gysling | |
| 6,691,584 B2 | 2/2004 | Gysling et al. | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 2002/0062681 A1 * | 5/2002 | Livingston | 73/24.01 |
| 2002/0064331 A1 | 5/2002 | Davis et al. | |
| 2003/0089161 A1 | 5/2003 | Gysling | |
| 2003/0136186 A1 | 7/2003 | Gysling | |
| 2003/0154036 A1 | 8/2003 | Gysling et al. | |
| 2004/0016284 A1 | 1/2004 | Gysling et al. | |

OTHER PUBLICATIONS

"Two Decades of Array Signal Processing Research, The Parametric Approach", H. Krim and M. Viberg, IEEE Signal Processing Magazine, Jul. 1996, pp. 67-94.

"Development of an array pressure sensors with PVDF film, Experiments in Fluids 26", Jan. 8, 1999, Springer-Verlag.

Multiplexed Fiber Bragg Grating Strain-Sensor System with a Fiber Fabry-Perot Wavelength Filter, A.D. Kersey, T.A. Berkoff, and W.W. Morey, Aug. 15, 1993, vol. 18, No. 16 Optics Letters.

U.S. Appl. No. 60/402,491, filed Aug. 2002, Gysling et al.

* cited by examiner

APPARATUS AND METHOD FOR MEASURING MULTI-PHASE FLOWS IN PULP AND PAPER INDUSTRY APPLICATIONS

CROSS-REFERENCE TO RELATED APPLICATIONS

This patent application claims the benefit of U.S. Provisional Patent Application Ser. No. 60/402,491, entitled "Fluid Measurement Device for Paper and Pulp Industry Sensing Applications" filed on Aug. 8, 2002, which is incorporated herein by referenced in its entirety.

TECHNICAL FIELD

This invention relates to apparatus and method for measuring parameters of a multi-phase flow, such as pulp slurries, in the paper and pulp industries. The parameters of the multi-phase flow include sound speed and density, which are used either independently or in conjunctions to determine the composition/consistency of multi-phase flow, including pulp and liquid slurries.

BACKGROUND ART

Slurries typical of the paper and pulp industry are mostly water and typically contain between 1% and 10% pulp content by mass. Monitoring the flow rate and consistency of the slurry can lead to improved quality and efficiency of the paper production process. The paper and pulp industry is currently evaluating and adopting a variety consistency meters. These prior art consistency meters include shear force measurement devices, both blade type and rotating type, optical measurement devices, including reflection, transmission and peak methods, and nuclear, microwave, ultrasound, and pressure differencing.

In addition, electromagnetic flow meters are the most widely used flow meter technology in the paper and pulp industry. The ability of various flow metering technology to monitor slurry flow rate reliability and accurately is challenged by the corrosive and erosive properties of the slurry. The approach described herein can be implemented on a non-intrusive basis and is therefore well-suited to the harsh environment posed by the paper and pulp slurries.

SUMMARY OF THE INVENTION

Objects of the present invention include a flow meter for measuring the composition/consistency of a multi-phase mixture such as slurries in pipes in pulp and paper industrial sensing applications.

According to the present invention, a flow meter for determining the composition of a multi-phase mixture flowing through a pipe includes a first apparatus that measures the speed of sound propagating through the multi-phase mixture at a first sensing region along said pipe that provides a first effective sound speed signal. A second apparatus measures the speed of sound propagating through the multi-phase mixture at a second sensing region along said pipe that provides a second effective sound speed signal. A signal processor, responsive to said first and said second effective sound speed signals, provides a parameter signal indicative of the composition of the multi-phase mixture within the pipe.

According to the present invention, a flow meter for determining the composition of a multi-phase mixture flowing through a pipe includes a first sensor head that includes a first array of pressure sensors that measures the speed of acoustic pressure waves propagating through the multi-phase mixture at a first sensing region along said pipe that provides first sensed acoustic pressure signals. A second apparatus includes a second array of pressure sensors that measures the speed of the acoustic pressure waves propagating through the multi-phase mixture at a second sensing region along said pipe that provides second sensed acoustic pressure signals. A signal processor, responsive to said first and said second sensed acoustic pressure signals, determines a parameter signal indicative of the composition of the multi-phase mixture.

According to the present invention, a method for use in an industrial sensing process for measuring the composition of a multi-phase mixture propagating through a pipe includes measuring a first effective sound speed at a first sensing region along said pipe and providing a first effective sound speed signal. A second effective sound speed is measured at a second sensing region along said pipe and providing a second effective sound speed signal. The composition is calculated using said first and said second effective sound speed signals.

The foregoing and other objects, features and advantages of the present invention will become more apparent in light of the following detailed description of exemplary embodiments thereof.

BEST MODE FOR CARRYING OUT THE INVENTION

Figure 1:
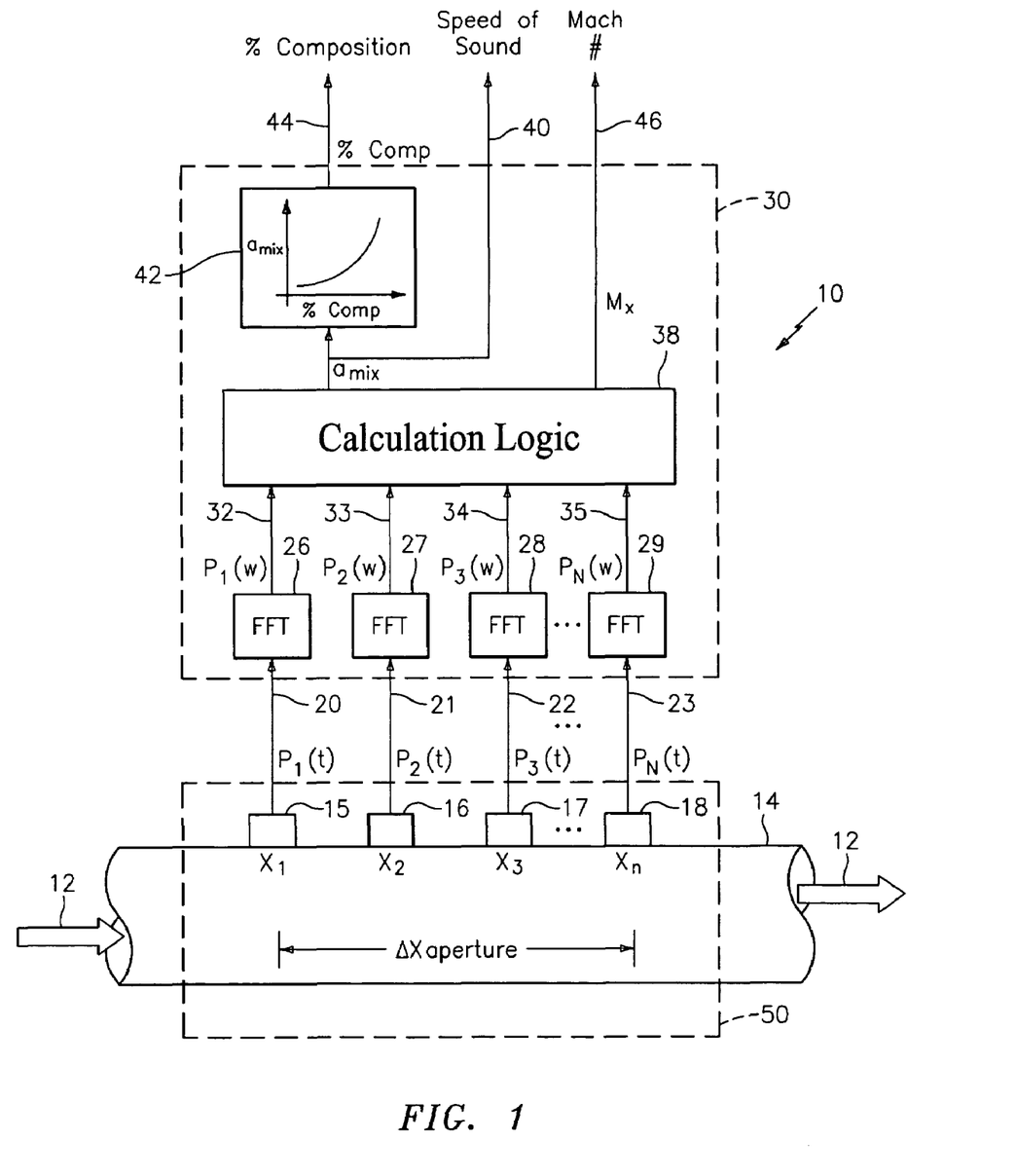
FIG. 1 is a schematic block diagram of a consistency meter, in accordance with the present invention.

Referring to FIG. 1, a flow meter 10 is provided that measures a number of parameters/characteristics of a multi-phase process flow 12, such as a pulp and liquid slurry, in a pulp and paper industry application. The flow meter is configured and programmed to measure the speed of sound propagating through the process flow within a pipe. The flow meter can measure at least the density and the composition/consistency (volumetric phase fraction) of the fluid/mixture flow 12. To determine any one of these parameters, the flow meter 10 measures the unsteady pressures created by the acoustic waves propagating through the mixture 12 flowing in the pipe 14 to determine the speed of sound (SOS), which will be described in greater detail hereinafter.

As described hereinbefore, the flow meter 10 is be configured and programmed to measure and process the detected unsteady pressures $P_1(t)$–$P_N(t)$ created by acoustic waves propagating through the mixture to determine composition of the mixture flow 12. One such flow meter 10 is shown in FIG. 1 that measures the speed of sound (SOS) of one-dimensional sound/acoustic waves propagating through the multi-phase process flow 12, namely the liquid/pulp ratio of the mixture. It is known that sound propagates through various mediums at various speeds in such fields as SONAR and RADAR fields. The speed of sound propagating through a mixture 12 within a pipe 14 may be determined using a number of known techniques, such as those set forth in U.S. patent application Ser. No. 09/344,094, entitled "Fluid Parameter Measurement in Pipes Using Acoustic Pressures", filed Jun. 25, 1999, and U.S. patent application Ser. No. 10/007,749, entitled "Fluid Parameter Measurement in Pipes Using Acoustic Pressures", filed Nov. 7, 2001, U.S. patent application Ser. No. 10/376,427, entitled "Apparatus and Method for Measuring Parameters of a Mixture Having Liquid Droplets Suspended in a vapor Flowing in a Pipe", filed Feb. 26, 2003, U.S. patent application Ser. No. 10/349,716, entitled "Apparatus and Method for Measuring Parameters of a Mixture Having Solid Particles Suspended in a Fluid Flowing in a Pipe", filed Jan. 23, 2003 and U.S. Pat. No. 6,587,798 issued Jul. 1, 2003, entitled "Method and System for Determining the Speed of Sound in a Fluid with a Conduit", each of which are incorporated herein by reference. The present invention utilizes at least one flow meter 10 to determine various parameters of the multi-phase mixture 12, wherein one of the parameters is the speed at which sound travels within the mixture pipe system as will be more fully described herein below.

In accordance with the present invention, the speed of sound propagating through the mixture 12 is measured by passively listening to the flow with an array of unsteady pressure sensors to determine the speed at which one-dimensional compression waves propagate through a multi-phase mixture 12, such as a pulp slurry, contained within the pipe 14.

As shown in FIG. 1, the flow meter 10 has a sensor head 50 comprising an array of at least three acoustic pressure sensors 15,16,17, located at three locations $X_1, X_2, X_3$ axially along the pipe 14. One will appreciate that the sensor array may include more than three pressure sensors as depicted by pressure sensor 18 at location $X_N$, or as few as two sensors. The pressure generated by the acoustic waves may be measured through holes in the pipe 14 ported to external pressure sensors 15–18 or by other techniques discussed hereinafter. The pressure sensors 15–18 provide pressure time-varying signals $P_1(t), P_2(t), P_3(t), P_N(t)$ on lines 20,21, 22,23 to a signal processing unit 30 to known Fast Fourier Transform (FFT) logics 26,27,28, 29, respectively. The FFT logics 26–29 calculate the Fourier transform of the time-based input signals $P_1(t)$–$P_N(t)$ and provide complex frequency domain (or frequency based) signals $P_1(\omega), P_2(\omega), P_3(\omega), P_N(\omega)$ on lines 32,33,34,35 indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

The frequency signals $P_1(\omega)$–$P_N(\omega)$ are fed to $a_{mix}$—Mx Calculation Logic 38 which provides a signal to line 40 indicative of the speed of sound propagating through the pulp slurry 12 $a_{mix}$ (discussed more hereinafter). The $a_{mix}$ signal is provided to map (or equation) logic 42, which converts $a_{mix}$ to a percent composition of the pulp slurry 12 and provides a % Comp signal to line 44 indicative thereof (as discussed hereinafter). Also, if the Mach number Mx is not negligible and is desired, the calculation logic 40 may also provide a signal Mx to line 46 indicative of the Mach number Mx.

More specifically, for planar one-dimensional acoustic waves in a homogenous mixture, it is known that the acoustic pressure field P(x,t) at a location x along a pipe, where the wavelength λ of the acoustic waves to be measured is long compared to the diameter d of the pipe 12 (i.e., λ/d>>1), may be expressed as a superposition of a right traveling wave and a left traveling wave, as follows:

$$P(x,t)=(Ae^{-ik_r x}+Be^{+ik_l x})e^{i\omega t} \qquad \text{Eq. 1}$$

where A,B are the frequency-based complex amplitudes of the right and left traveling waves, respectively, x is the pressure measurement location along a pipe, ω is frequency (in rad/sec, where ω=2πf), and $k_r, k_l$ are wave numbers for the right and left travelling waves, respectively, which are defined as:

$$k_r \equiv \left(\frac{\omega}{a_{mix}}\right)\frac{1}{1+M_x} \text{ and } k_l \equiv \left(\frac{\omega}{a_{mix}}\right)\frac{1}{1-M_x} \qquad \text{Eq. 2}$$

where $a_{mix}$ is the speed of sound of the mixture in the pipe, ω is frequency (in rad/sec), and $M_x$ is the axial Mach number of the flow of the mixture within the pipe, where:

$$M_x \equiv \frac{V_{mix}}{a_{mix}} \qquad \text{Eq. 3}$$

where Vmix is the axial velocity of the mixture. For non-homogenous mixtures, the axial Mach number represents the average velocity of the mixture and the low frequency acoustic field description remains substantially unaltered, which may use to determine the volumetric flow provided the cross-sectional area of the pipe is known.

The data from the array of sensors may be processed in any domain, including the frequency/spatial domain, the temporal/spatial domain, the temporal/wave-number domain or the wave-number/frequency (k-ω) domain. As such, any known array processing technique in any of these or other related domains may be used if desired.

Also, some or all of the functions within the signal processing unit 30 may be implemented in software (using a microprocessor or computer) and/or firmware, or may be implemented using analog and/or digital hardware, having sufficient memory, interfaces, and capacity to perform the functions described herein.

Acoustic pressure sensors 15–18 sense acoustic pressure signals that, as measured, are lower frequency (and longer wavelength) signals than those used for ultrasonic flow meters of the prior art, and thus the current invention is more tolerant to inhomogeneities in the flow.

In addition, the present invention incorporates the compliance of the pipe 14 to determine the effective speed of sound. The acoustic pressure signals $P_1(t)$–$P_N(t)$ are generated within the pulp slurry 12 of the pipe 14 by a variety of non-discrete sources such as remote machinery, mills, fans, valves, elbows, as well as the process flow 12 itself. It is this last source, the process flow 12 flowing within the pipe 14, which is a generic source of acoustic noise that assures a minimum level of acoustics for any pulp and paper piping system for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the flow meter 10 passively listens to the mixture flow 12, the present invention contemplates adding an acoustic source to inject a desired acoustic wave into the flow to be measured, such as by compressing, vibrating and/or tapping the pipe, to name a few examples.

Assuming that the pulp exhibits negligible slip (both steady and unsteady), the sound speed can be assumed to be non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

Including the effect of the compliance introduced by the conduit 12 (in this case a circular pipe of modulus E, radius R and wall thickness t)

$$\frac{1}{\rho_{mix} a_{measured}^2} = \frac{1}{\rho_{mix} a_{mix}^2} + \sigma \text{ where } \sigma \equiv \frac{2R}{Et}$$

Figure 2:
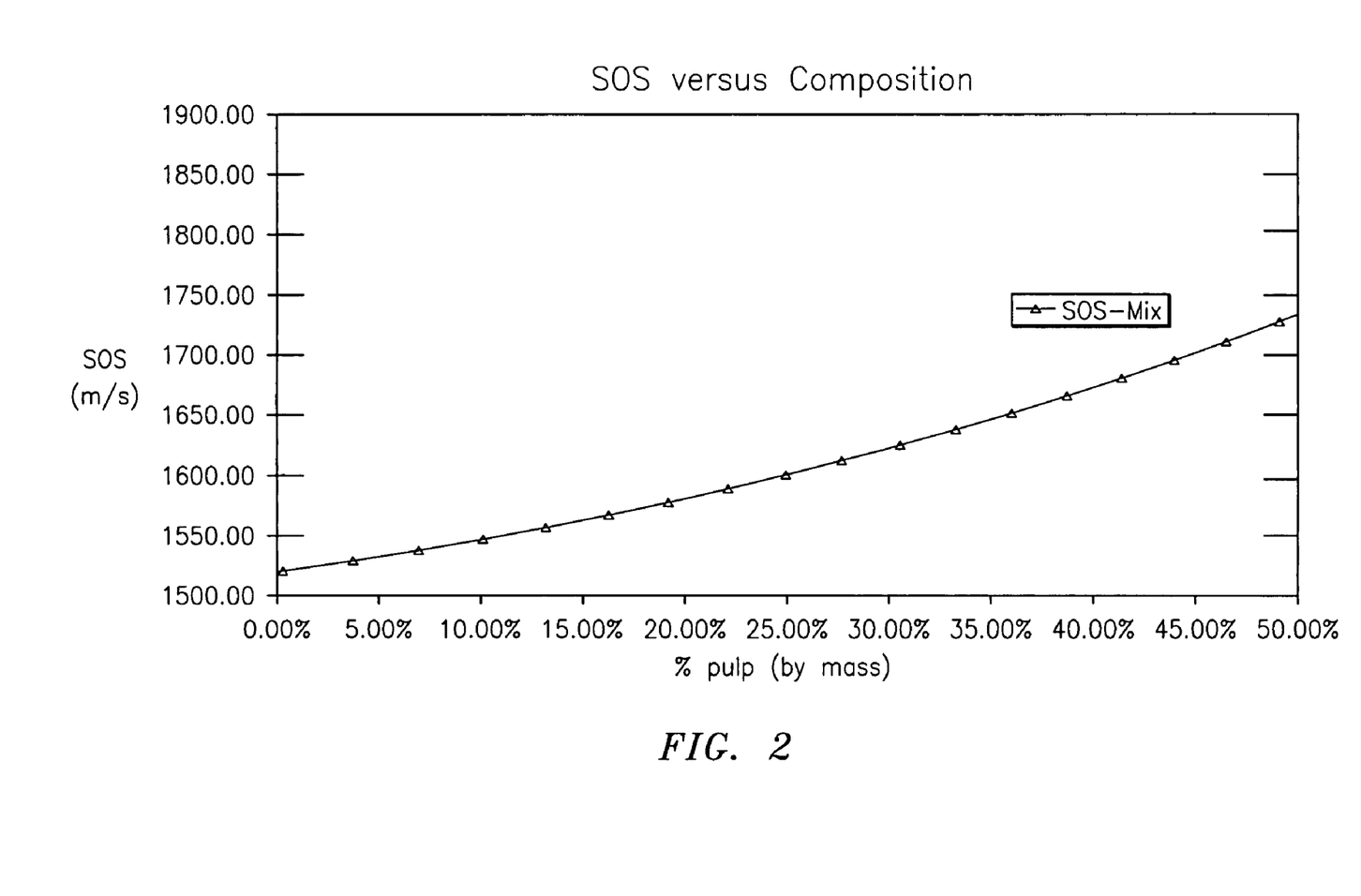
FIG. 2 is a graphical representation of the speed of sound (SOS) propagating through a pulp slurry over various consistencies on a mass percentage basis, in accordance with the present invention.

Utilizing the relations above, the speed at which sound travels within the piping system of a representative pulp slurry is shown in FIG. 2 as a function of the percentage of pulp (or composition). For example, assuming that the sound speed of the water is 1524 m/sec, sound speed of the pulp is 3000 m/sec, density of water is 1000 kg/m³ and the density of the pulp is 1400 kg/m³, the sound speed of the mixture is plotted in FIG. 2 for pulp contents of 0% to 50% by mass. Consistency or composition is typically defined as the mass ratio of the solids to the fluid.

Figure 3:
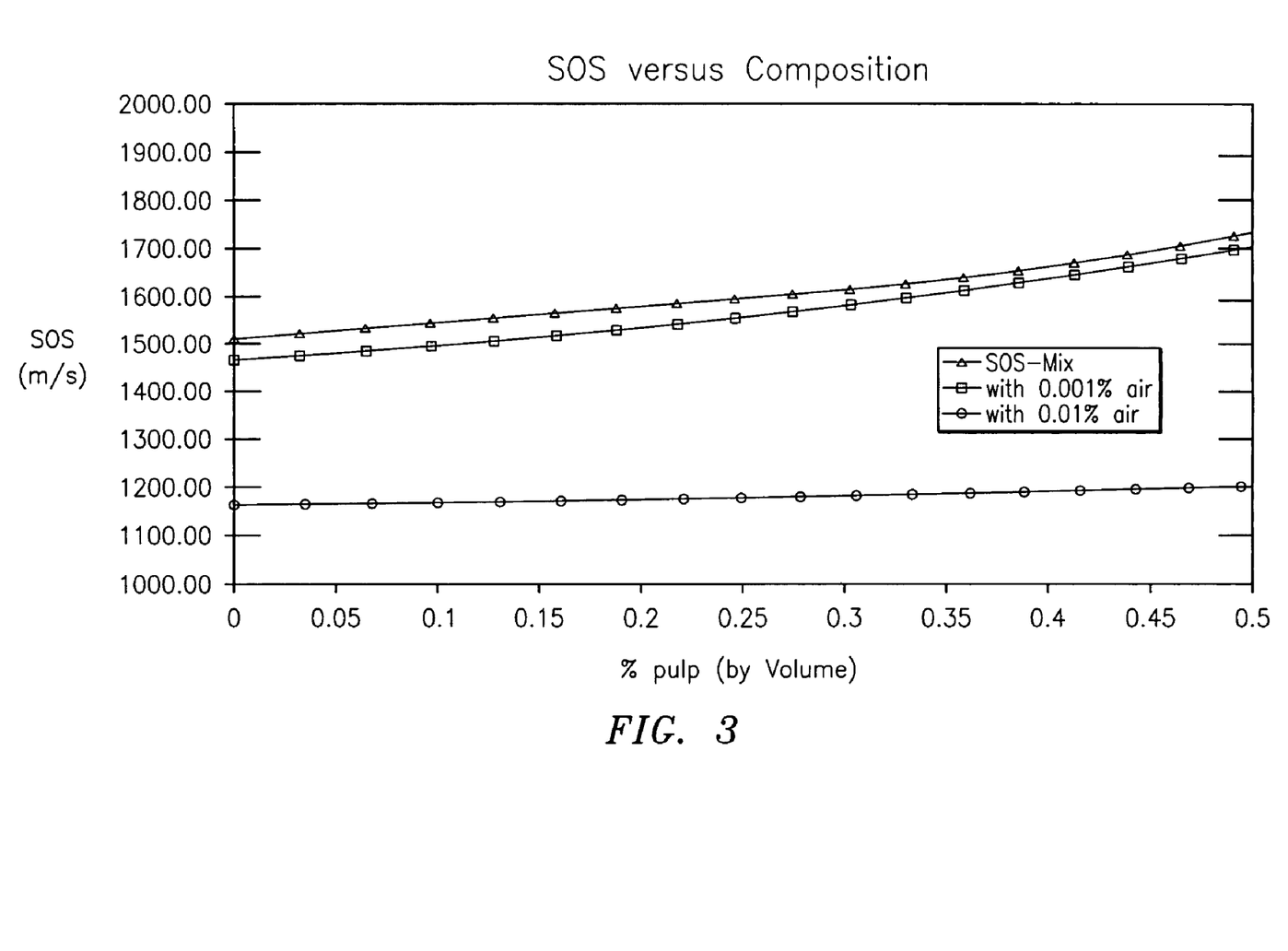
FIG. 3 is a graphical representation of the speed of sound (SOS) propagating through a pulp slurry over various consistencies on a volumetric percentage basis at various percentage of entrained air, in accordance with the present invention.

Thus, sound speed is related to the composition of the mixture and thus, an appropriately interpreted sound speed measurement could be used to provide a measure of consistency. However, the sound speed of predominately liquid mixtures is typically very sensitive to small amounts of entrained air, particularly for mixture operating a near ambient pressure. Therefore, although conceptually there is link between consistency and sound speed, a small but unknown and fluctuating quantity of air in the mixture would render a sound speed measurement difficult to interpret in terms of consistency. To illustrate this, FIG. 3 shows the sound speed versus consistency for the example described above with out any air and that for the same mixture with a trace amounts (0.001% and 0.01% by volume) of air. As shown, the amount of air contained in the mixture has a dominant effect. The conduit and fluid properties can be used determine information regarding the fluid contained within the conduit—specifically, the density of the fluid.

To counter this sensitivity to air and or other unknowns regarding the relationship between mixture sound speed and composition in slurries, the relationship between fluid density, sound speed and conduit compliance can be exploited to measure the density of the fluid within a pipe using the sound speed measured in two sections of the conduit with different, but constant, cross sectional area compliances.

The flow meter 100, embodying the present invention, utilizes the speed at which sound 130 propagates through the process flow 12 (i.e., pulp slurry) within a conduit or pipe 112 to determine compositional information of the pulp slurry. Compositional information is provided through the interpretation of the speed of sound itself, as well as the effect of conduit properties on the propagation velocity of the flow.

In accordance with the present invention, the sound speed is measured using an array of pressure transducers 110, similar to that described hereinbefore. For a two component mixture, the measured sound speed can be used to determine the volumetric phase fraction of the two components utilizing relationships of the density and sound speed of the two components and the compliance properties of the conduit.

The sound speed (α) propagating through a mixture 12 and the density (ρ) of the mixture can be related to volumetric phase fraction ($\phi_i$) of the components through the Wood equation.

$$\frac{1}{\rho_{mix} a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves 130 propagating within a fluid/mixture 12 contained within a conduit 112 exert an unsteady internal pressure loading on the conduit. The degree to which the conduit displaces as a result of the unsteady pressure loading influences the speed of propagation of the compression wave 130. For a given fluid/mixture 12, the more compliant the conduit, the greater the reduction of the propagation velocity. Also, for a given pipe 112 stiffness, the denser the fluid and the higher the infinite volume sound speed, the greater the reduction in the speed of sound due to the pipe flexibility. The following description of the present invention describes how these relationships can be utilized to determine the density and/or composition of slurries 12 used in the paper and pulp industry.

Figure 4:
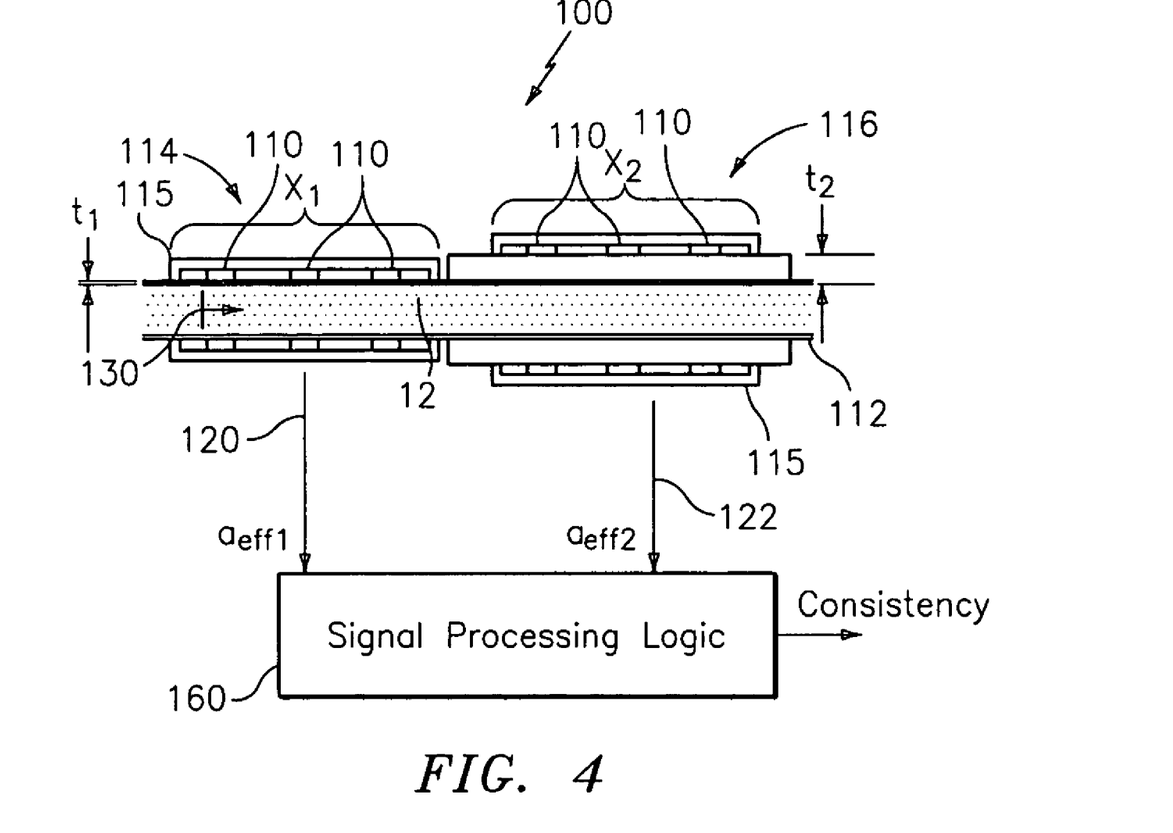
FIG. 4 is a schematic block diagram of another consistency meter having two sensing regions with different cross-sectional area compliancy, in accordance with the present invention.

The meter 100 in FIG. 4 using a pair of sound speed meters 114,116, similar to the flow meter 10 of FIG. 1 described hereinbefore, placed at axial locations, or sensing regions, X1, X2 along the pipe 112, measures the density of pulp slurry 12 in the pipe. The sound speed meters 114,116 provide the effective speed of sound $a_{1eff}$ and $a_{2eff}$ of the fluid/pipe system on lines 120,122 which are provided to signal processing logic 160 which determines the density and thereby the consistency of the pulp slurry 12 in the pipe 112 using relationships between the compliance of the pipe and various fluid parameters as will be more fully described herein below. While the embodiment of the present invention shown in FIG. 4 includes a pair of signal processing units 30 (see FIG. 1) and a signal processing logic 160 (see FIG. 4), the present invention contemplates a single processing unit that provides all the signal processing of processing units 30 and 160 combined.

Also, some or all of the functions within the logic 160 may be implemented in software (using a microprocessor or computer) and/or firmware, or may be implemented using analog and/or digital hardware, having sufficient memory, interfaces, and capacity to perform the functions described herein.

The effective speeds of sound $a_{1eff}$ and $a_{2eff}$ are provided to logic 160 wherein the logic calculates the density of the fluid by the difference in the effective sound speeds as will be more fully described herein below. Sound speed meters 114, 116 utilize acoustic pressure signals that, as measured, are lower frequency (and longer wavelength) signals than those used for ultrasonic flow meters of the prior art, and thus the current invention is more tolerant to inhomogeneities in the flow. In addition, the present invention differs from prior art fluid parameter measurement devices in that the present invention incorporates the compliance of the pipe 112 to determine the effective speed of sound of the pipe/fluid system. The typical frequency range for acoustic pressure signals of the present invention is from about 10 Hz to about 10,000 Hz. The acoustic pressure signals are generated within the fluid 12 of the pipe 112 by a variety of non-discrete sources such as remote machinery, pumps, valves, elbows, as well as the fluid flow itself. It is this last source, the fluid flowing within the pipe, that is a generic source of acoustic noise that assures a minimum level of acoustics for any fluid piping systems for which the present invention takes unique advantage. The flow generated acoustics increase with mean flow velocity and the overall noise levels (acoustic pressure levels) are a function of the generating mechanism and the damping mechanism. Experience indicates that pipe systems typically have sufficient ambient noise levels of 100 to 180 dbA.

No external discrete noise source is required within the present invention and thus may operate using passive listening, however an active sound source ma be provided such a vibrator, tapping device and/or an acoustic noise generator. It is within the scope of the present that the sound meter or sensor 114, 116 spacing may be known or arbitrary and that as few as two sensors are required if certain information is known about the acoustic properties of the system as will be more fully described herein below.

It is an important aspect of the present invention that one-dimensional, planar compression waves 130 (e.g., acoustic wave) propagating within a fluid contained within a conduit 112 exert an unsteady internal pressure loading on the conduit. The degree to which the conduit displaces as a result of the unsteady pressure loading influences the speed of propagation of the compression wave 130 within the context of the fluid/pipe system. For a given fluid, the more compliant the conduit, the greater the reduction of the propagation velocity of the compression wave. Also, for a given pipe stiffness, the denser the fluid and the higher the infinite volume sound speed, the greater the reduction in the speed of sound due to the pipe flexibility or compliance.

The relationship among the infinite domain speed of sound ($a_{mix\,\infty}$) and density ($\rho_{mix}$) of a fluid/mixture the elastic modulus of the pipe (E), thickness of the pipe (t), and radius of a vacuum-backed cylindrical conduit (R), the effective propagation velocity ($a_{eff}$) for a one dimensional compression wave is given by the following expression:

$$a_{eff} = \frac{1}{\sqrt{1/a_{mix\infty}^2 + \rho_{mix}\frac{2R}{Et}}} \quad \text{(eq 1)}$$

It is important to note that the term vacuum backed as used herein refers to a situation in which the fluid surrounding the conduit externally has negligible acoustic impedance compared to that of the fluid internal to the pipe. For example, a consistency meter containing a typical water and pulp slurry immersed in air at standard atmospheric conditions satisfies this condition and can be considered "vacuum-backed" 115.

Equation 1 can be generalized in terms of the cross-sectional area compliance ($\sigma$) of the conduit and that of the fluid 12. The cross sectional area compliance is a measure of the increase in normalized cross-sectional area of a conduit 112 for a given increase in internal pressure.

$$\frac{1}{\rho_{eff} a_{eff}^2} = \frac{1}{\rho_{mix} a_{mix\infty}^2} + \sigma_{conduit} \quad \text{(eq 2)}$$

$$\sigma_{conduit} = \frac{\partial \tilde{A}_{crosssection}}{\partial P} \quad \text{(eq 3)}$$

Where $\tilde{A}$ is the perturbation in the cross sectional area normalized by the nominal cross sectional area. For a vacuum-backed, circular cross-section pipe of elastic modulus E, radius R, and wall thickness t, the conduit compliance is given by:

$$\sigma_{conduit} = \frac{2R}{Et} \quad \text{(eq 4)}$$

Defining $\alpha$ as the ratio of conduit compliance in the "soft" section of the meter to that of the "stiff" section of the meter, density of the fluid within meter can be expressed as, where $\sigma_2$ is the cross sectional area compliance of the stiff section (section 2 in FIG. 4) of the meter:

$$\rho_{mix} = \frac{1}{(\alpha-1)\sigma_2}\left(\frac{1}{a_{eff1}^2} - \frac{1}{a_{eff2}^2}\right)$$

It is important to note that, in general, the cross section area compliance of the fluid/pipe system can be a complex function of frequency and amplitude and can depend on all elements acoustically coupled to the conduit 112. For example, if an additional fluid surrounded the conduit, the acoustic properties of the surrounding fluid would influence the cross section area compliance presented to the compressional waves 130 propagating internal to the conduit. It is for this reason that the present invention is presented in embodiments having a vacuum backed shell surrounding the sound speed meters 114,116 as described herein above.

In accordance with the present invention, using the relationships described herein above, the dependence of propagation speed of compression disturbances (one dimensional, planar compression acoustic waves) on the compliance of the conduit 112 and fluid properties (such as sound speed and density) can be used to determine information regarding the fluid contained within the conduit, specifically, the consistency/composition of the fluid/mixture.

Referring again to FIG. 4, there is shown a consistency meter 100 in which the speed of sound propagating through the pulp slurry 12 of unknown consistency is measured within two regions $X_1$, $X_2$, wherein the pipe 112 has differing cross section area compliances associated with the two regions. A first effective speed of sound $a_{eff1}$ of the fluid/pipe system is determined from an array of pressure measurements provided by sensors 110 of sound speed meter 114. A second speed of sound $a_{eff2}$ of the fluid/pipe system is determined from an array of pressure measurements provided by sensors 110 of sound speed meter 116. As will be more fully described herein below, the change in propagation velocity of one dimensional acoustic waves 130 between the two regions $X_1$, $X_2$, along with knowledge of the cross sectional compliances of each section, provides a means to determine the density of the multi-phase fluid 12. As illustrated in this example, the variation in the system cross sectional compliance could be achieved through a change of the conduit compliance, namely in the form of a change in wall thickness of the pipe 112. Other methods to vary the system cross sectional compliance are described below, and any known method of varying the system cross sectional compliance is contemplated by the present invention.

The expression for the change in effective speed of sound between two sections of vacuum-backed conduit differing only in wall thickness, where $a_0$ is the speed of sound of the fluid 12 and $\rho_0$ is the density of the fluid is given by:

$$a_{eff_1} - a_{eff_2} = \frac{1}{\sqrt{1/a_0^2 + \rho_o \frac{2R}{Et_1}}} - \frac{1}{\sqrt{1/a_0^2 + \rho_o \frac{2R}{Et_2}}} \quad (eq\ 5)$$

In accordance with the present invention, the density of the unknown fluid 12 is determined by measuring two effective system sound speeds in two regions with differing, but known structural properties. For example, in the cylindrical pipe 112 of FIG. 4 having a thickness $t_1$ and $t_2$ and elastic modulus E, the density $\rho_{mix}$ of the unknown slurry is given by:

$$\rho_{mix} = \left(\frac{1}{a_{eff_1}^2} - \frac{1}{a_{eff_2}^2}\right)\frac{E}{2R}\frac{t_1 t_2}{t_2 - t_1} \quad (eq\ 6)$$

As discussed herein above, varying wall thickness is but one way to achieve a change in system cross sectional area compliance and thereby provide a density measurement in accordance with the present invention. In general, the larger the change in system cross sectional area compliance between the two (or more regions) in which the sound speed is measured, the more robust the density measurement. In addition, an increase in the number of regions, i.e. greater than two, along a pipe 112 with varying compliance in which system sound speeds are measured would give additional, redundant measurements of density. The additional data could yield a more robust or accurate overall system depending on the specific application.

Figure 5:
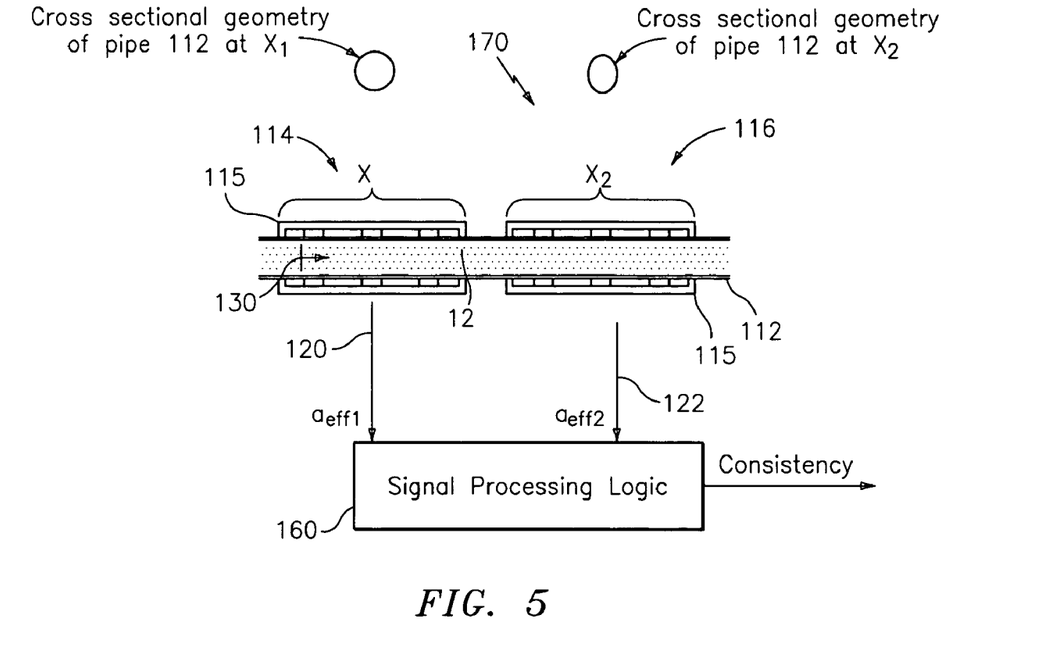
FIG. 5 is a schematic block diagram of a consistency meter having an egg shaped cross section in one sensing region and a round cross-section in another sensing region, in accordance with the present invention.

One alternative method to achieve large variations in system 170 compliance by changing the conduit compliance is best shown with reference to FIG. 5 wherein a first sensing region in surrounding $X_1$ comprises a circular cross section conduit and second sensing region surrounding $X_2$ comprises a non-circular cross section conduit, shown as an egg-shaped conduit by way of example, all other properties of the pipe 112 remaining equal. The circular geometry surrounding $X_1$ represents, for a given cross section, material modulus, and wall thickness, the configuration with the lowest cross sectional area compliance. However, the geometry of the cross section of the modified sensing region surrounding $X_2$, such as by modifying or "egging" the circular section into an oval (or other alternative shapes such as using cross section possessing flattened sides) significantly increases the compliance of the conduit 112. In certain embodiments between sensing region $X_2$ (non-circular geometry) and sensing region $X_1$ (circular geometry) of the same wall thickness t, cross sectional area compliance ratios greater than 30 are achievable. As demonstrated in the figures referenced herein above, increasing the compliance ratio of the pipe increases the sensitivity of the consistency meter 100 by increasing the system compliance ratio thereby increasing the change in effective system sound speed for a given fluid density.

Figure 6:
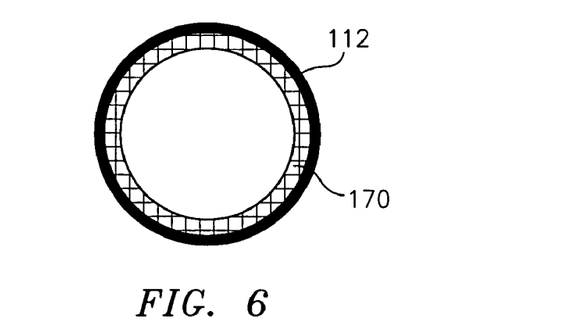
FIG. 6 is a cross sectional representation of an embodiment of a consistency meter having a closed cell foam liner, in accordance with the present invention.

The effective system cross sectional area compliance can be modified in a variety of manners such as, by way of example, varying materials, incorporating wall treatments, resonators or cavities. Referring to FIG. 6 there is shown a modified system cross sectional compliance technique wherein a closed cell foam 170 (or other compressible liner material) is positioned along the walls of one of the sensing sections of the pipe 112 thereby modifying the effective compliance of that section of pipe. In the embodiment shown in FIG. 6, the pipe/fluid interface would be defined as the inner surface of the liner. An increase in fluid pressure would increase the effective cross sectional area of the fluid by both compressing the foam 170 and by expanding the pipe 112. It is also contemplated by the present invention that the two sensing regions may be comprised of different material types or any other variation in geometry or material property that would effectuate a difference in the compliance of the pipe between the two sensing regions.

Referring again to FIG. 4, as discussed hereinbefore, and defining a as the ratio of conduit compliance in the "soft" section, sensing region $X_1$, of the consistency meter 100 to that of the "stiff" section, sensing region $X_2$, of the meter, and where $\sigma_2$ is the cross sectional area compliance of sensing region $X_2$ of the meter, the density of the fluid $\rho_{mix}$ within the meter can be expressed as:

$$\rho_{mix} = \frac{1}{(\alpha - 1)\sigma_2}\left(\frac{1}{a_{eff_1}^2} - \frac{1}{a_{eff_2}^2}\right) \quad (eq\ 7)$$

Figure 7:
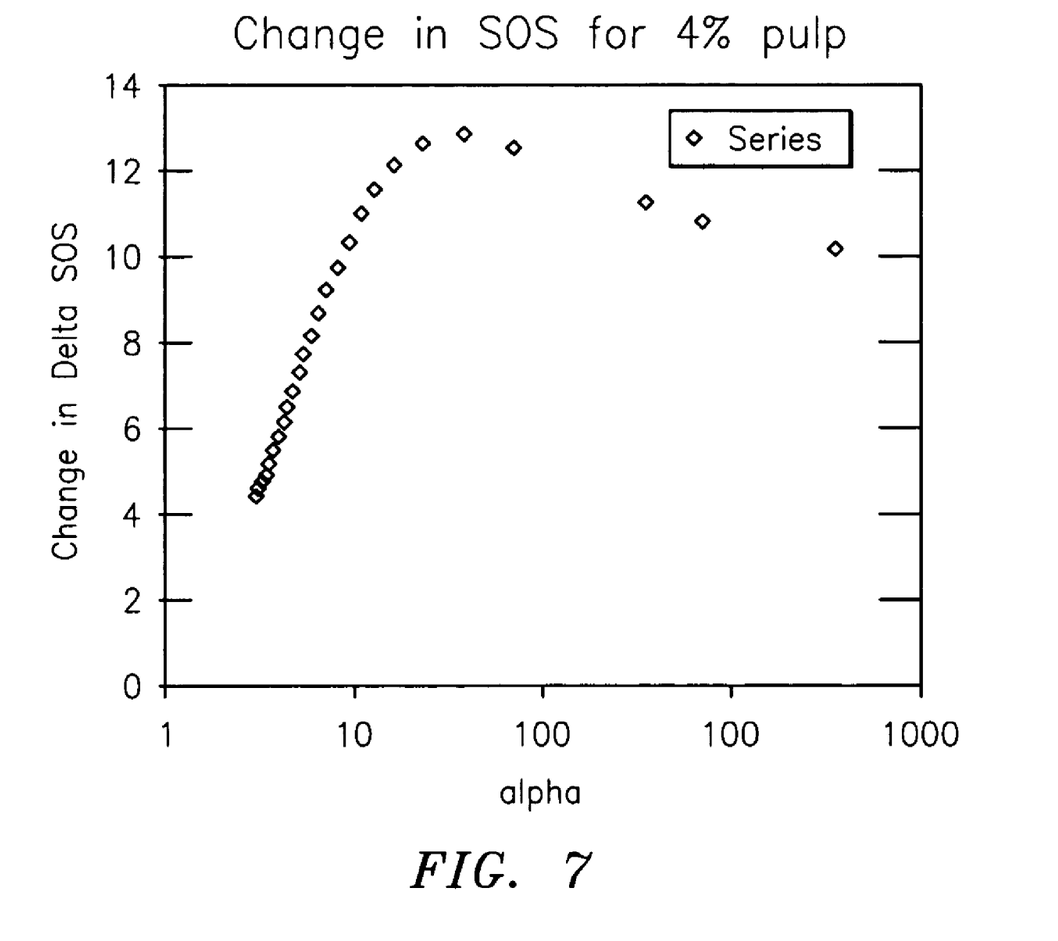
FIG. 7 is a graphical representation of the change in the delta sound speed between the hard and soft section for a 4% change on volumetric pulp content for slurry, in accordance with the present invention.

Selecting the compliance ratio parameter α is an important design consideration. FIG. 7 is illustrative of the method of determining the optimum compliance ration when designing the sensing sections $X_1, X_2$ of the present invention. FIG. 7 shows the change in the delta sound speed between the hard and soft sections $X_1, X_2$ for a 4% change on volumetric pulp content for slurry described above. Generally, it is preferable to have the maximum delta sound speed for a given percentage of pulp composition. In this example in FIG. 7, the greatest delta sound speed change is approximately 13 m/sec between that for a 0% pulp to that of a 4% pulp mixture when the compliance ratio of the two sensing regions is approximately 40. While the relationship between measured sound speeds, conduit compliance and density is given above and not directly related to this metric, the change in delta sound speed is a useful meter and maximizing this metric should result in good system performance.

Figure 8:
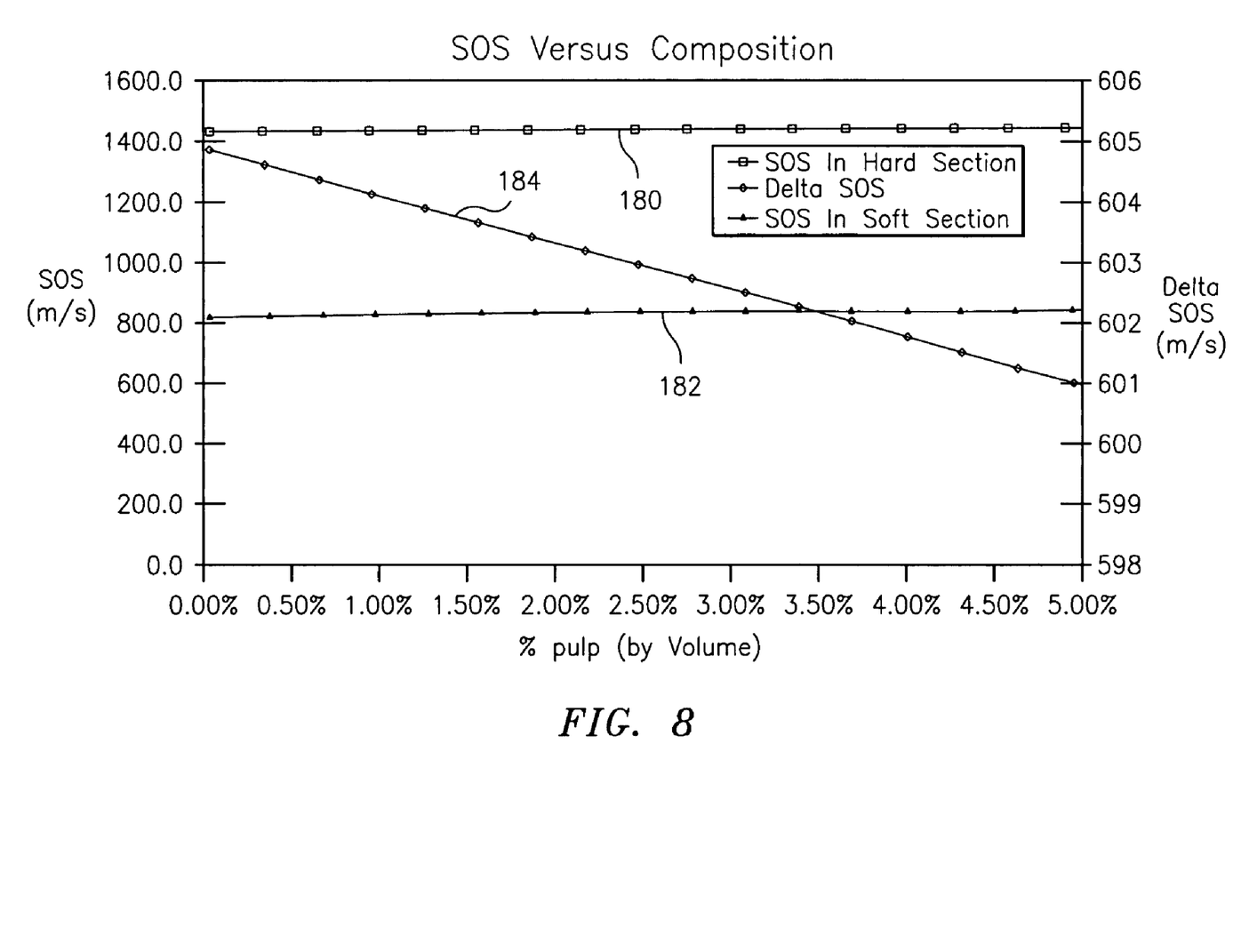
FIG. 8 is a graphical representation of the measured sound speeds in the hard and soft sections and the difference in sound speed between the two sections for a range of pulp loading between 0% and 5%, in accordance with the present invention.

FIG. 8 shows the measured speed of sound (SOS) in the hard section 180 and the measured speed of sound (SOS) in the soft section 182. Further, FIG. 8 shows the difference (or delta) in sound speed between the hard and soft sections 184. Each of this plots are over a range of pulp loading between 0% and 5% for a consistency meter with a compliance ratio of 40. As shown, the nominal difference in sound speed is quite substantial, approximately 600 m/secs between the propagation velocities in the two sections.

Figure 9:
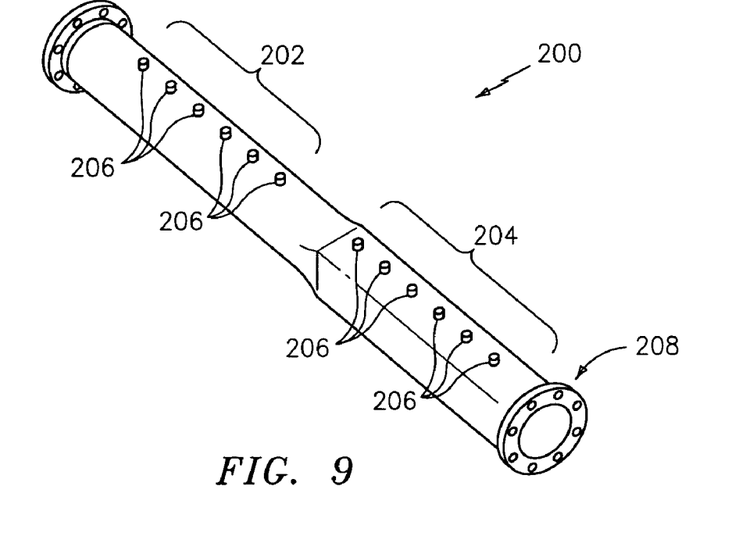
FIG. 9 is a perspective view of an embodiment of a consistency meter including a round cross-section in one sensing region and a square cross-section in another sensing region, in accordance with the present invention.

FIG. 9 shows the sensing portion of the pipe 208 of an alternative embodiment 200 for the consistency meter 100 described herein. The pipe of the consistency meter 200 includes a round section 202 and a square section 204 to provide different cross-sectional area compliance. Pressure ports are shown to accept conventional electronic unsteady pressure transducers 206, enabling a sound speed measurement in each section. For this example, the round section is a 6 inch schedule 80 pipe section. The overall length of each section, the spacing and number of sensors, is dependent on application constraints, cost constraints and performance requirements. In this example, the square section 204 is 5.4 inches square with a 1.0 inch bend radius on each corner with 0.250 inch wall thickness. Each section is stainless steel. The resulting consistency meter 200 has a compliance ratio of 40 between the round (stiff) section and the square (soft) section. Based on the design methodology outline herein, the embodiment would result in a consistency meter effective for paper and pulp applications.

It should be note that the contrast in compliance between each section can be achieved in a number of ways. Wall thickness and cross section geometry examples have been discussed herein. Another feasible approach is to use fiberglass section of pipe. Typically, the elastic modulus of fiber reinforced pipe is approximately 10–100 time lower than steel. Thus for identical geometry sections, a steel/fiberglass consistency meter will have a compliance ratios in effective range the range of 10–100.

In operation and referring again to FIG. 4, the two sound speed meters 114, 116 provide effective system sound speeds $a_{1\mathit{eff}}$ and $a_{2\mathit{eff}}$ to signal processing logic 160, which includes the relationship set forth in equation 7. The compliance of the conduit $\sigma_2$ in the second sensing region $X_2$ and the ratio of the compliances between the two sections $\sigma_1/\sigma_2$ are further provided to logic 160 to calculate the consistency of the slurry based on the density of the mixture $\rho_{mix}$. It is an important aspect of the present invention that the consistency of the fluid mixture can be determined without requiring specific speed of sound and calibration information on the fluid itself. In the embodiments described thus far it is only required that the sound speed and consistency of the fluid itself is the same in the two section. Thus, although the consistency measurement described herein is based on speed of sound measurements, no knowledge of the sound speed of the fluid is required to determine consistency.

As shown, effectiveness of the consistency meters 100, 170, 200 of the present invention described herein scales with both the ratio of the compliances of the two conduit sections as well as with the ratio of the compliance of conduit to that of the fluid mixture 12. Thus, the consistency meter of the present invention is more effective when the system cross sectional compliance contributed by the conduit 112 is a significant fraction of that contributed by the fluid and the ratio of the system cross sectional compliance of the two regions is significantly greater than one.

The pressure sensors described herein may be any type of pressure sensor, capable of measuring the unsteady (or ac or dynamic) pressures within a pipe, such as piezoelectric, optical, capacitive, piezo-resistive (e.g., Wheatstone bridge), accelerometers, velocity measuring devices, displacement measuring devices, etc. If optical pressure sensors are used, the sensors 18–24 may be Bragg grating based pressure sensors, such as that described in copending U.S. patent application Ser. No. 08/925,598, entitled "High Sensitivity Fiber Optic Pressure Sensor For Use In Harsh Environments", filed Sept. 8, 1997, now U.S. Pat. No. 6,016,702. Alternatively, the sensors 18–24 may be electrical or optical strain gages attached to or embedded in the outer or inner wall of the pipe which measure pipe wall strain, including microphones, hydrophones, or any other sensor capable of measuring the unsteady pressures within the pipe 12. In an embodiment of the present invention that utilizes fiber optics as the pressure sensors 18–24, they may be connected individually or may be multiplexed along one or more optical fibers using wavelength division multiplexing (WDM), time division multiplexing (TDM), or any other optical multiplexing techniques (discussed more hereinafter).

Any other technique or configuration for an optical strain gage may be used. The type of optical strain gage technique and optical signal analysis approach is not critical to the present invention, and the scope of the invention is not intended to be limited to any particular technique or approach.

Referring to FIGS. 1, 4 and 5, a piezo-electronic pressure transducer may be used (or alternatively even a common strain gage may be used) as one or more of the pressure sensors and it may measure the unsteady (or dynamic or ac) pressure variations $P_{in}$ inside the pipe 112 by measuring the pressure levels (or for the strain gage, the elastic expansion and contraction of the diameter of the pipe 112. In an embodiment of the present invention the sensors comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics may used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants.

Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 12. The sensors may alternatively be removable or permanently attached via known mechanical techniques such as mechanical fastener, spring loaded, clamped, clamshell arrangement, taping, pressure sensitive adhesives, strapping or other equivalents. Alternatively, the strain gages, including optical fibers and/or gratings, may be embedded in a composite pipe. If desired, for certain applications, the gratings may be detached from (or strain or acoustically isolated from) the pipe 112 if desired.

Furthermore the present invention contemplates that each of the pressure sensors 15–18 of the flow meter 10 may include a piezoelectric sensor 104–107 that provides a piezoelectric sheet material 110 to measure the unsteady pressures of the fluid/particle mixture 12. The piezoelectric material, such as the polymer, polarized fluoropolymer, polyvinylidene fluoride (PVDF), measures the strain induced within the process pipe 112 due to unsteady pressure variations within the process mixture 12. Strain within the pipe is transduced to an output voltage or current by the attached piezoelectric sensors.

The PVDF sheet material may be adhered to the outer surface of a steel strap that extends around and clamps onto the outer surface of the pipe 112. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc., which is incorporated herein by reference. The advantages of this technique include non-intrusive flow rate measurements, low cost, measurement technique requires no excitation source (ambient flow noise is used as an acoustic source), and higher temperatures.

Although the invention has been described with respect to the detection of certain types of unsteady flow fields and the pressure disturbances associated therewith, it should be understood that the invention will also detect any unsteady stochastic flow field and its associated pressure field that propagates within the flow, provided the spatial filters have a separation within the acceptable coherence length of the flow field to be measured and the sensor spacing within each spatial filter is longer than a characteristic spatial length of the disturbance. Some examples of such other stochastic flow fields are gas bubbles, gas slugs, particles, or chunks of material, which may travel in the flow at different rates than the mean flow velocity, thereby creating a traveling pressure disturbance, which exhibits a velocity slip between it and the other constituents in the mixture.

Figure 10:
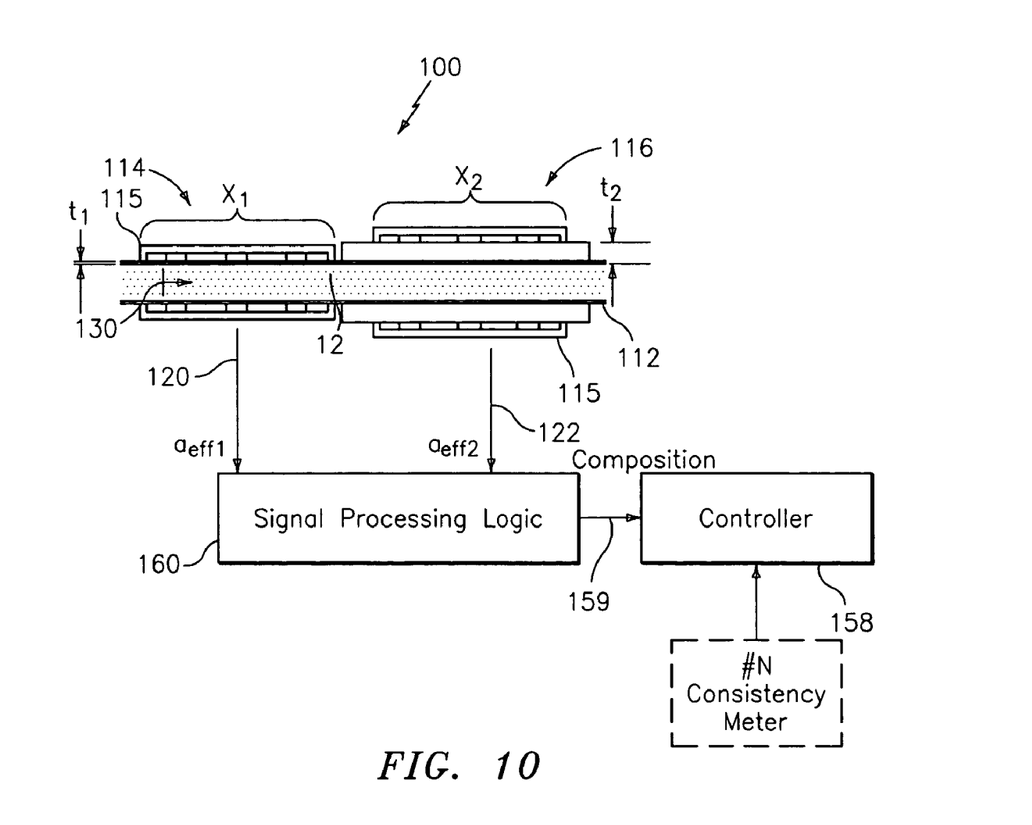
FIG. 10 is a schematic block diagram of consistency meter and a monitoring/controller system, in accordance with the present invention.

A plurality of the consistency meters 100 of the present invention of FIG. 4 may be connected to a common cable and multiplexed together with other consistency meters (as shown in FIG. 10) using any known multiplexing technique. For instance, it is contemplated that the various embodiments of the consistency meter 100 of the present invention include the capability of being multiplexed as well as capable of communication with various protocols and systems currently in use in the industrial sensing area. For instance, and with reference to FIG. 10 there is shown a portion of a process control incorporating a consistency meter 100 in accordance with the present invention with a controller 158. Signal processing logic 160 communicates composition, density and/or volumetric flow along line 159 to control device 158, a computer or micro-processor for example, where the information may be used to control the fluid characteristics in pipe 112 through known controls means such as a pump, valve, throttle, etc. (not shown). In certain embodiments of the control system shown and with appropriate electro-optical conversion within signal processing logic 160 of the sensor return signal to a conventional 4–20 mA signal the signal can be combined with other control devices and sensors at control device 158 via separate electrical lines. In this particular embodiment the communication from the fiber optic sensor is performed with a 4–20 mA analog signal, and the open protocol HART®. (Highway Addressable Remote Transducer) digital communications format. Similarly, communication from the fiber optic consistency meter 100 may also be performed with open and interoperable protocol FOUNDATION™ Fieldbus that provides a digital communication link among intelligent field level and control devices via electrical lines. The control device 158 can be configured for use with other process protocols, including Device Bus, Sensor Bus, Profibus, the ethernet, and others in use throughout the world. For instance, a typical paper/pulp process control system that utilizes electronic consistency meters of the prior art requires an electrical process loop to facilitate both a power signal to the transmitters and bi-directional communication, and can be constructed in accordance with a number of the aforementioned process communication protocols.

It is important to note that the operation of the flow measurement devices described herein above may be used alone or in various combinations to achieve a variety of results without departing from the scope of the present invention.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. A meter for determining the mass ratio of the solids of a multi-phase mixture flowing through a pipe, said meter comprising:
a first meter that measures the speed of sound propagating through the multi-phase mixture at a first sensing region along said pipe which provides a first effective sound speed signal;
a second meter that measures the speed of sound propagating through the multi-phase mixture at a second sensing region along said pipe which provides a second effective sound speed signal;
wherein said first sensing region along the pipe has a first compliance and said second sensing region along the pipe has a second compliance, and wherein said first compliance is different from said second compliance to change the speed of sound from the first sensing region to the second sensing region; and
a signal processor, responsive to the difference of said first and said second effective sound speed signals, that determines a parameter signal indicative of the mass ratio of solids of the multi-phase mixture within the pipe.

2. The meter of claim 1, wherein said first and said second meters determine said first and said second effective sound speeds from acoustic pressure waves traveling axially through the multi-phase mixture flowing within the pipe.

3. The meter of claim 2, wherein the acoustic pressure waves are provided by a passive acoustic source.

4. The meter of claim 2, wherein the acoustic pressure waves are one dimensional.

5. The meter of claim 2, wherein the acoustic pressure waves are inherently provided by the multi-phase mixture flowing through the pipe.

6. The meter of claim 1, wherein the multi-phase mixture has at least three components, wherein one of the components is a gas.

7. The meter of claim 6, wherein the signal processor determines the phase fraction of pulp of a pulp slurry having entrained gas.

8. The meter of claim 1, wherein said first and said second sensing region of said pipe comprises different cross sectional geometry.

9. The meter of claim 8, wherein at least one of said cross sectional geometry comprises a non-circular cross sectional geometry.

10. The meter of claim 1, wherein the pipe at the first and second sensing regions have different cross sectional area compliance.

11. The meter of claim 1, wherein the thickness of the wall of the first and second sensing regions of the pipe are different.

12. The meter of claim 1, wherein one of the first and second sensing regions of the pipe is lined to provide different compliances.

13. The meter of claim 1, wherein the first meter includes a first array of sensors for measuring acoustic pressure waves propagating through the multi-phase mixture, and wherein the second meter includes a second array of sensors for measuring acoustic pressure waves propagating through the multi-phase mixture.

14. The meter of claim 13 further comprising at least one concentric shell positioned around at least one of said first and said second array of sensors thereby acoustically isolating said first and second array of sensors from an outside environment.

15. The meter of claim 13, wherein the sensors are disposed on the exterior of the pipe.

16. A meter for determining the mass ratio of solids of a multi-phase mixture flowing through a pipe, said meter comprising:
a first meter that measures the speed of acoustic pressure waves propagating through the multi-phase mixture at a first sensing region along said pipe which provides first sensed acoustic pressure signals;
a second meter that measures the speed of the acoustic pressure waves propagating through the multi-phase mixture at a second sensing region along said pipe which provides second sensed acoustic pressure signals;
wherein said first sensing region along the pipe has a first compliance and said second sensing region along the pipe has a second compliance, and wherein said first compliance is different from said second compliance to change the speed of sound from the first sensing region to the second sensing region; and
a signal processor, responsive to said first and said second sensed acoustic pressure signals, that determines the difference between a first effective sound speed signal and a second effective sound speed signal to determine a parameter signal indicative of the mass ratio of solids of the multi-phase mixture.

17. The meter of claim 16, wherein the multi-phase mixture has at least three components, wherein one of the components is a gas.

18. The meter of claim 17, wherein the signal processor determines the phase fraction of pulp of a pulp slurry having entrained gas.

19. The meter of claim 16, wherein the signal processor determines said first and said second effective sound speeds from acoustic pressure waves traveling axially through the multi-phase mixture flowing within the pipe.

20. The meter of claim 19, wherein the acoustic pressure waves are one dimensional.

21. The meter of claim 19, wherein the acoustic pressure waves are inherently provided by the multi-phase mixture flowing through the pipe.

22. The meter of claim 16, wherein said first and said second sensing regions of said pipe comprises different cross sectional geometry.

23. The meter of claim 22, wherein at least one of said cross sectional geometry comprises a non-circular cross sectional geometry.

24. The meter of claim 16, wherein the pipe at the first and second sensing regions have different cross sectional area compliance.

25. The meter of claim 16, wherein the thickness of the wall of the first and second sensing regions of the pipe are different.

26. The meter claim 24, wherein one of the first and second sensing regions of the pipe is lined.

27. The meter of claim 16, wherein the acoustic pressure waves are provided by a passive acoustic source.

28. The meter of claim 27, wherein the sensors are disposed on the exterior of the pipe.

29. A method for measuring the mass ratio of solids of a multi-phase mixture propagating through a pipe; the method comprising:
measuring a first effective sound speed at a first sensing region along said pipe and providing a first effective sound speed signal;

measuring said a second effective sound speed at a second sensing region along said pipe and providing a second effective sound speed signal;

wherein said first sensing region along the pipe has a first compliance and said second sensing region along the pipe has a second compliance, and wherein said first compliance is different from said second compliance to change the speed of sound from the first sensing region to the second sensing region;

determining a differential signal indicative of the difference between the first effective sound speed signal and the second effective sound speed signal; and determining a parameter signal indicative of said mass ratio of solids in response to the differential signal.

30. The method of claim 29, wherein the multi-phase mixture has at least three components, wherein one component is a gas.

31. The method of claim 30, wherein the mass ratio of pulp of a pulp slurry having entrained gas is determined.

32. The method of claim 29, wherein said first and said second meters determine said first and said second effective sound speeds from acoustic pressure waves traveling axially through the multi-phase mixture flowing within the pipe.

33. The method of claim 32, wherein the acoustic pressure waves are one dimensional.

34. The method of claim 32, wherein the acoustic pressure waves are inherently provided by the multi-phase mixture flowing through the pipe.

35. The method of claim 29, wherein said steps of measuring said first and said second effective sound speeds comprises measuring a strain of the pipe.

36. The method of claim 29, wherein the cross sectional shape of the first and second sensing regions are different.

37. The method of claim 29, wherein the thickness of the wall of the first and second sensing regions of the pipe are different.

38. The method of claim 29, wherein the measuring the first effective sound speed includes:

measuring acoustic pressure waves propagating through the multi-phase mixture using a first array of pressure sensors; and wherein the measuring the second effective sound speed includes:

measuring acoustic pressure waves propagating through the multi-phase mixture using a second array of pressure sensors.

* * * * *